(12) United States Patent
Scholz et al.

(10) Patent No.: US 8,133,277 B2
(45) Date of Patent: Mar. 13, 2012

(54) MEDICAL DEVICE FOR FLUID FLOW AND METHOD OF FORMING SUCH DEVICE

(75) Inventors: Hans Scholz, Berlin (DE); Karen Petzold, Berlin (DE); Ulf Kruger, Berlin (DE)

(73) Assignee: Bard Peripheral Vascular, Inc., Tempe, AZ (US)

( * ) Notice: Subject to any disclaimer, the term of this patent is extended or adjusted under 35 U.S.C. 154(b) by 966 days.

(21) Appl. No.: 11/665,891

(22) PCT Filed: Oct. 21, 2005

(86) PCT No.: PCT/EP2005/011351
§ 371 (c)(1), (2), (4) Date: Jun. 20, 2007

(87) PCT Pub. No.: WO2006/045555
PCT Pub. Date: May 4, 2006

(65) Prior Publication Data
US 2008/0172121 A1      Jul. 17, 2008

(30) Foreign Application Priority Data
Oct. 21, 2004    (GB) .................................. 0423422.5

(51) Int. Cl.
*A61F 2/02*    (2006.01)
*A61F 2/06*    (2006.01)
*A61F 2/24*    (2006.01)
*A61F 2/04*    (2006.01)
*A61M 1/10*    (2006.01)

(52) U.S. Cl. ...................... 623/11.11; 623/1.1; 623/1.28; 623/1.3; 623/1.32; 623/2.1; 623/3.1; 623/23.64

(58) Field of Classification Search .................. 604/266, 604/264, 48, 523, 93.01; 623/1.13, 1.3, 1.23, 623/1.39, 901, 1.1, 1.24, 1.26, 1.28, 1.32, 623/1.52, 2.1, 3.1, 11.11, 23.64, 23.69; 138/37
See application file for complete search history.

(56) References Cited

U.S. PATENT DOCUMENTS
2,375,180 A  * 5/1945 Vigo ............................... 417/151
(Continued)

FOREIGN PATENT DOCUMENTS
DE          19945009 A1       1/2001
(Continued)

OTHER PUBLICATIONS

Gunther et al.; "Two Alternative Models Concerning the Perialveolar Microcirculation in Mammalian Lungs"; Biol. Res. 38: 49-54, 2005.
(Continued)

*Primary Examiner* — Kevin C Sirmons
*Assistant Examiner* — Shefali Patel
(74) *Attorney, Agent, or Firm* — Rutan & Tucker, LLP

(57) ABSTRACT

A medical device which defines a lumen for flowing a bodily fluid from an upstream end of the device to a downstream end thereof is disclosed. The device has a luminal wall (14) that extends between the upstream and downstream ends and defines the lumen within which the fluid flows. The wall exhibits a succession of protuberances spaced from each other along the length of the device. Each protuberance has a flank facing upstream (54) and a flank facing downstream (64), the flank facing upstream extending into the fluid flow so that a radially outermost part of the flow of fluid from the upstream to the downstream end of the device impinges on the upstream flank and is thereby caused to reverse its flow, and flow upstream from the upstream flank to the downstream flank of the next adjacent protuberance upstream, creating micro-vortices between two adjacent protuberances.

31 Claims, 6 Drawing Sheets

U.S. PATENT DOCUMENTS

| | | | |
|---|---|---|---|
| 3,453,359 A | | 7/1969 | Clement et al. |
| 3,731,711 A | * | 5/1973 | Bauer .......................... 138/178 |
| 3,908,704 A | | 9/1975 | Clement et al. |
| 4,486,312 A | * | 12/1984 | Slingsby et al. .............. 210/656 |
| 5,108,417 A | * | 4/1992 | Sawyer ....................... 623/1.22 |
| 5,344,425 A | | 9/1994 | Sawyer |
| 5,718,713 A | | 2/1998 | Frantzen |
| 5,769,815 A | * | 6/1998 | Utterberg ........................ 604/80 |
| 6,217,764 B1 | * | 4/2001 | Bellhouse ................ 210/321.69 |
| 6,312,452 B1 | | 11/2001 | Dobak, III et al. |
| 6,312,463 B1 | * | 11/2001 | Rourke et al. .............. 623/1.39 |
| 6,883,471 B1 | * | 4/2005 | Belter et al. ................ 123/41.74 |
| 7,445,592 B2 | * | 11/2008 | Pecor ............................. 600/16 |
| 2002/0045932 A1 | | 4/2002 | Israel |
| 2002/0179166 A1 | | 12/2002 | Houston et al. |
| 2003/0139806 A1 | | 7/2003 | Haverkost et al. |
| 2003/0139807 A1 | | 7/2003 | Houston et al. |
| 2003/0144572 A1 | * | 7/2003 | Oschman et al. ............... 600/16 |
| 2004/0033364 A1 | | 2/2004 | Spiridigliozzi et al. |
| 2004/0037986 A1 | | 2/2004 | Houston et al. |
| 2004/0039351 A1 | | 2/2004 | Barrett |
| 2005/0010169 A1 | * | 1/2005 | Kuhlein et al. ............ 604/93.01 |
| 2005/0055085 A1 | * | 3/2005 | Rivron et al. ................ 623/1.39 |
| 2006/0259128 A1 | * | 11/2006 | Pavcnik et al. ............. 623/1.24 |

FOREIGN PATENT DOCUMENTS

| | | |
|---|---|---|
| EP | 0973462 A1 | 1/2000 |
| EP | 1139917 A2 | 10/2001 |
| EP | 1194712 A1 | 4/2002 |
| EP | 1254645 A1 | 11/2002 |
| EP | 1314406 A2 | 5/2003 |
| EP | 1343433 A2 | 9/2003 |
| EP | 1399200 A1 | 3/2004 |
| FR | 2657945 A3 | 8/1991 |
| GB | 862795 A | 3/1961 |
| GB | 2382776 A | 6/2003 |
| GB | 2384189 A | 7/2003 |
| JP | 63065908 A | 3/1988 |
| WO | 9315661 A1 | 8/1993 |
| WO | 9421362 A1 | 9/1994 |
| WO | 0010623 A1 | 3/2000 |
| WO | WO 00/38591 | 7/2000 |
| WO | WO 01/04532 | 1/2001 |
| WO | 0230327 A2 | 4/2002 |
| WO | 02100454 A1 | 12/2002 |
| WO | 03045279 A1 | 6/2003 |
| WO | 03045280 A1 | 6/2003 |
| WO | 03103540 A1 | 12/2003 |
| WO | 03103736 A1 | 12/2003 |

OTHER PUBLICATIONS

Kinlay et al.; "Coronary Flow Velocity and Disturbed Flow Predict Adverse Clinical Outcome After Coronary Angioplasty"; Arterioscler. Thromb. Vasc. Biol., Aug. 2002; 22: 1334-1340.

Dec. 22, 2005 International Search Report in international application No. PCT/EP2005/011351 filed on Oct. 21, 2005.

Dec. 22, 2005 Written Opinion of the International Searching Authority in international application No. PCT/EP2005/011351 filed on Oct. 21, 2005.

Apr. 24, 2007 International Preliminary Report on Patentability in international application No. PCT/EP2005/011351 filed on Oct. 21, 2005.

Feb. 2, 2005 Great Britain Search Report in GB application No. GB0423422.5 filed on Oct. 21, 2004.

* cited by examiner a)

b)

c)

a)

b)

c)

MEDICAL DEVICE FOR FLUID FLOW AND METHOD OF FORMING SUCH DEVICE

PRIORITY

This application is a national stage application under 35 USC 371 of International Patent Application No. PCT/EP2005/011351, filed Oct. 21, 2005, claiming priority to United Kingdom Patent Application No. GB 0423422.5, filed Oct. 21, 2004, each of which is incorporated by reference into this application as if fully set forth herein.

FIELD OF THE INVENTION

The present invention relates to medical devices which define a lumen for flowing a bodily fluid from an upstream end of the device to a downstream end thereof. More particularly, the present invention relates to medical devices which define a lumen for flowing blood and which have a wall surface that inhibits adhesion of material out of the bodily fluid onto the wall surface of the lumen.

BACKGROUND OF THE INVENTION

Disturbance of arterial blood circulation is one of the most common diseases in industrial countries. Mostly, the cause of this disease is arteriosclerosis, which leads to a constriction or even occlusion of the artery. Modern medicine treats highly localised occlusions by catheter expansion (percutaneous transluminal angioplasty) and possibly placement of a stent. Lengthier occlusions, predominantly at the leg and at the heart, are by-passed by a natural or artificial vessel (bypass-surgery). The ideal vessel-replacement material for arteries having small calibers (about 4 to 6 mm) is the particularly suitable v. saphena magna (skin deep long main vein at the leg). This vein often is not available because of preceding varicosity surgery or it is not suitable to be implanted for other reasons. In case the patient's own vein cannot be used, the implantation of an artificial vessel (prothesis) becomes necessary.

The present inventor has a professional interest in the success of surgical procedures in which, if no bodily vein is available, a tubular implant such as a graft, graft-stent or stent is placed in a part of the (cardio-) vascular system of a patient. A complicating factor of this kind of surgical procedures is that the range of materials for the implants is relatively small and, within this range, materials are prone to occlusion due to adhered, coagulated blood (thrombosis). As soon as blood has adhered to the wall of a tubular implant and is coagulated, there will be no possibility for removal of the coagulated blood, the lumen likely to be occluded after a certain period of time. The risk of thrombosis is particularly high for artificial blood vessels with relatively small diameters (up to about 7 mm). Since thrombosis is life-threatening, occlusion of the artificial blood vessels must be avoided, which is up to now managed by the use of drugs (anticoagulants).

Grafts are usually longer than stents, and, therefore, in general the danger of occlusions is significantly higher for grafts. Grafts may have a length between about 20 mm and about 800 mm, the diameters of the grafts depending on the intended application and being within a range of about 2 mm to about 30 mm. Smaller graft diameters are for instance needed for bypasses to the foot artery or the knee-joint artery, whereas larger diameters are needed for aortocoronary bypasses. Grafts with diameters less than about 2 mm have not yet been artificially realized.

The thrombogenic effect of artificial blood vessels is known in the state of the art. There are a large number of disclosures, which discuss the surface topography of the luminal walls of bodily prostheses. These documents teach to increase the blood flow velocity while eliminating or reducing any kind of turbulent flow, see for instance U.S. Pat. No. 5,108,417 or WO 00/38591.

The creation of (quasi-) turbulent flow is suggested in WO 01/04532, a disclosure relating to industrial conduits and conduit elements. This disclosure contains no hint or suggestion to apply its teaching to medicine and to surfaces having contact with blood, such as bodily implants. The document is in relation to a surface topography on the inner wall of a conduit that will generate a turbulent or quasi-turbulent boundary layer between the inner wall of the conduit and the main flow of the medium. This specific topography is said to enhance the capacity of the conduit to entrain in the fluid flow particles which are disposed on the wall of the conduit.

Trying to find a way to reduce the thrombogenicity of artificial blood vessels, the present inventor has noticed that natural surfaces in lumens of the human body are seldom completely smooth. Yet, the flow of fluid through these lumens is laminar, rather than turbulent, more or less everywhere in the body (the chambers of the heart are an obvious exception), because in general turbulent flow will irritate the inner walls of vessels.

Subsequent to these findings, the present inventor has conducted extensive investigations and experimentation with a view to discovering whether one can learn from the natural topography of lumens in the body so as in some way to inhibit adherence of particles from blood, and, in consequence, render thrombosis less likely.

In particular, experimentation with streamline visualization and cine filming, in channels with various patterns of wall surface topography, has revealed a possible mechanism and explanation that offers exciting possibilities to inhibit adherence of particles from blood on inner walls of medical devices.

The mechanism is based on the classic distribution of flow velocity across the transverse cross section of a lumen such as a tube in which laminar flow is occurring which is known in the field of fluid dynamics. This classic distribution shows a parabolic flow profile having a maximum velocity along the central axis of the lumen, and a velocity which steadily falls, as one moves from the center of the lumen to the wall of the lumen, with the fluid which is in contact with the wall of the lumen having a zero velocity (see FIG. 1 below in which the vertical axis denotes flow velocity and the horizontal axis denotes the inside diameter d of a tube with a lumen of radius r and a circular cross-section centered on a long axis 0). It is believed that laminar flow occurs in various vessels and such laminar flow can be inferentially determined based on a dimensionless Reynolds number "Re" where Re=average velocity times the vessel inside diameter times the density of blood divided by the viscosity of blood. The Reynolds number of blood flow varies depending on the types of vessel and the location of the vessel within a mammalian body. For example, a study entitled "Two alternative Models Concerning the Perioaveoloar Microcirculation in Mammalian Lungs" by BRUNO GÜNTHER[a], ENRIQUE MORGADO[b,c*] and MANUELA COCINA (available at http://www.scielo.cl/scielo.php?pid=S0716-97602005000100007&script=sci_arttext&tlng=en) indicates that Reynolds number Re for laminar vs. turbulent flow in the case of microcirculation, is about 0.03 in the arterioles, and about 0.0025 in the systemic capillaries, in contrast with the blood flow in the aorta, where Re=2349. In another study, "Coronary Flow Velocity and Disturbed Flow Predict Adverse Clinical Outcome After Coronary Angioplasty" by Kinlay et al., (available online at http://atvb.ahajournals.org/cgi/content/full/22/8/1334#R14-112431 or from Scott Kinlay, MBBS, PhD, Cardiovascular Division, Brigham and Women's Hospital, 75 Francis Street, Boston, Mass. 02115, the flow of a liquid is laminar if the Reynolds number is <2000.

Related to blood this means a long retention period of the blood cells tending to adhesion at the luminal wall. Natural blood vessels exhibit an anti-thrombogenic surface and thereby prevent the adhesion of the blood cells that precipitates a complex cascade of events, which leads to coagulation of the blood (thrombosis) and occlusion of the vessel. Up to now, all materials known for manufacturing of artificial blood vessels have no anti-thrombogenic surface and, especially with small calibers (smaller than 7 mm), tend to promote deposition of blood cells with consequential coagulation and thereafter occlusion due to the coagulated blood. Thus, posits the inventor, there exists a direct correlation between the likelihood of thrombosis and the flow velocity in the marginal zone of an artificial blood vessel or artificial surfaces, which are in constant contact with blood, in general.

Accordingly, the inventor advocates a medical device which reduces the thrombogenic effect by increasing the flow velocity in the marginal zone of a lumen of a medical device thereby to reduce the retention time of blood cells prone to adhesion in the marginal zone and thereby rendering the possibility of a thrombosis less likely.

SUMMARY OF THE INVENTION

Aspects of the invention are defined in the independent claims below. The dependent claims are directed to optional and preferred features.

This invention relates to medical devices such as implants and tubing in which bodily fluid such as blood flows outside the body, e.g. in dialysis or in open heart surgery. The implants may be artificial vascular prostheses, modified natural grafts or artificial cardiac protheses. The invention is not restricted to a specific method of surgery, and the intracorporal devices of the present invention may for instance be implanted by open surgery, by catheter, with or without delivery system.

It is an object of the present invention to provide an improved medical device, whereby the medical device decreases the thrombogenic effect encountered especially when blood is in contact with artificial surfaces. Specifically, by placing on the wall surface of the medical device a succession of protuberances spaced from each other along the length of the device, the laminar flow pattern from the upstream and to the downstream end of the medical device having a lumen can be modified in the fluid flow layers adjacent to the luminal wall, in order to disturb the stasis of the layer adjacent to the luminal wall. More specifically, instead of stasis, it is proposed to stimulate the creation of micro-vortices in the marginal zone. Specifically, an upstream-facing flank surface of each protuberance intercepts that part of the general flow through the lumen of the medical device which is next to the wall, and reverses it, as the flow is turned from flowing downstream where it intercepts the tip of each protuberance, to flowing upstream by the time it has flown radially outwardly along the flank surface of the protuberance to reach the base of the protuberance, from which it flows upstream along the wall of a medical device until it reaches the downstream-facing flank of the next upstream adjacent protuberance (which turns it radially inwardly once again to join the general downstream flow of fluid radially inside the tip of that protuberance).

The reverse flow is caused by a pressure increase in the vicinity of each of the protuberances due to the flowing fluid being retained in the proximity of the luminal wall by the protuberances. This pressure increase causes on the one hand the successively flowing fluid (entering the lumen of the medical device) having a high flow velocity to be deflected by the protuberances. On the other hand, the fluid in the marginal zone, which has lost a major part of its velocity due to friction at the luminal wall, is forced to a back flow due to the pressure gradient acting against the flow. Thus, the reason for the creation of micro-vortices being a slowdown of the flow velocity in the vicinity of the protuberances causing a pressure increase. This increased pressure forces fluid layers close to the luminal wall, which have already been slowed down to a large extent by friction and thus not being able to act against the pressure increase, to a reverse flow.

Significant to note, in the context of bodily lumens, is that the counter-flow or reverse flow from downstream to upstream, between any two adjacent protuberances, is only caused in the marginal region so that the flow in the middle of the lumen does not constantly change its flow direction, but, rather, is always an unidirectional downstream flow (i.e. the overall flow can still be considered laminar from a physical point of view, because, as mentioned above, it is thought that bodily tissue reacts better to laminar than to turbulent flow).

The reader will appreciate that the spacing of the protuberances, which may be formed continuously or discontinuously, their height, and the particular shape of the upstream and downstream flank surface of each protuberance will be organized so as most efficiently to create the desired flow pattern between adjacent protuberances. The height of two adjacent protuberances may be the same or different, depending on the respective application. In a preferred embodiment, the height of each protuberance is about 1/10 of the outside diameter of the medical device. In particular, the height of each protuberance preferably is from about 0.02 to about 2 mm, more preferably from about 0.05 to about 1 mm.

As to the distance along the lumen between two adjacent protuberances, in a preferred embodiment the distance between two adjacent protuberances is from about 1 to about 10 times the height of the protuberance, more preferably from about 2 to about 6 times the height of the protuberance. The protuberances may be equidistantly spaced along the lumen and/or radially over the inner circumference of the medical device, or the distance between two adjacent protuberances may vary in the longitudinal and/or radial direction.

The shape of the upstream and the downstream flank of each protuberance may be the same or different, and regarding possible forms of the flanks, one envisages for instance either an essentially linear or concave shape, although the shape of the flanks is not limited to these examples, rather any shape which is suitable for the respective purpose can be used. The transition between the wall surface and the downstream and/or upstream flank of an arbitrary protuberance may, for instance, follow an exponential curve. Corners, angles and sharp transitions should be avoided here, because blood cells have an increased tendency to adhere to surfaces at sharp transition points, where flow is more likely to be stagnant or slower.

In addition, the protuberances, considered as macro-structures, may themselves be structured with a micro-structure in the form of micro-protuberances overlying the macro-structure. Preferably, the height of the micro-protuberances is from about 10 to about 50 μm, and the distance between two adjacent micro-protuberances is from about 20 to about 100

µm. In addition to said microstructures, or instead of the micro-structures, the protuberances may comprise a nano-structure. One example for a contemplated nano-structure are irregularities being considered responsible for the "Lotus-effect", which is known, per se.

Generally speaking, one needs a protuberance height that is big enough to set up the counter-flow, but not so big as to limit more than necessary the overall rate of transport of mass of fluid downstream through the medical device.

When there is natural formation of the luminal wall of a "conduit" in the body, the surface topography will likely be dependent on the flow direction, and exhibit a lack of symmetry between the upstream end and the downstream end of the bodily conduit. When realizing the present invention, in an implant with a luminal wall formed in accordance with the present invention, it may well also be the case that the protrusions are asymmetric, with the form of the upstream-facing flank differing from that of the downstream flank of each protuberance. In one preferred embodiment, the upstream flank has a shallower slope than the downstream flank. However, it may well be that a compromise can be reached, between on the one hand optimal performance in the body, and on the other hand efficiency in manufacture and placement in the body. An implant which is symmetrical as between its upstream and downstream end should be more economical to manufacture, and more tolerant and versatile, during its placement by a medical practitioner. In particular, when the upstream flank and the downstream flank have essentially the same slope, the medical practitioner does not have to pay attention in which direction the bodily implant has to be placed into the body.

As to methods of making medical devices such as implants in accordance with the present invention, in all methods a medical device is produced which defines a lumen for flowing a bodily fluid from an upstream end of the device to a downstream end thereof. All methods of the invention include the step of forming a wall surface which extends between the upstream and downstream ends and which defines a lumen in which the fluid flows. The desired macro-, micro- and/or nano-structures can either be formed in one step or in separate steps.

In one aspect of the present invention, a succession of protuberances is formed in the wall surface simultaneously with forming the wall itself, whereas in another aspect of the invention a succession of protuberances is formed in the wall surface subsequently to forming the wall. The medical devices may for instance be produced by continuous casting or extrusion processes, the protuberances e.g. being formed by using two counter-rotating forming tools. The tools can either be integrated into the machine conducting the forming process (such as an extruder), for forming the protuberances simultaneously with the overall device, or may be integrated in a separate machine, for forming the protuberances subsequently to forming the device as such.

Yet another aspect of the invention relates to forming a succession of protuberances in a material other than that constituting the medical device as such and adhering this material to the medical device. In this case, the succession of protuberances is formed in a material serving as "inlay" having a form which is suitable to be adhered to the medical device as such. For instance, should the medical device have the form of a tube, the inlay should as well be in the form of a tube, the outer diameter of the inlay being more or less same as the inner diameter of the medical device (within an acceptable tolerance). The inlay is then adhered to the medical device by any suitable technique, as for instance bonding, pressing, gluing etc. The form of the inlay, however, is not limited to bodies defining a lumen, but it can as well be a coating material such as a foil.

In still another aspect of the invention, the medical device is inverted for forming the protuberances and/or micro-protuberances. In one approach, protuberances are formed on the abluminal surface of a tube, which is then turned inside out, so that the protuberances are on the luminal surface. In another approach, the tube is first turned inside out, and then the protuberances are formed on the abluminal surface, after which the tube is inverted again, to put the protuberances on the luminal surface of the tube, such surface being of course the original luminal surface, prior to the two successive inversions of the tube.

As already described above for another production method, a material other than that constituting the medical device can be attached to the wall surface of the inverted prosthesis, e.g. a foil bearing the desired surface pattern. Otherwise, the protuberances can be formed in the material of the wall of the tube itself.

In general, the succession of protuberances can be formed by mechanical (e.g. cutting), thermal (e.g. heat accompanied shaping by pressing) and chemical (e.g. etching) processes. Regarding the outer form of the protuberances, one envisages forming the protuberances for instance in the shape of a continuous wave or helical thread during progressive continuous formation of the lumen by processes such as continuous casting or extrusion. If protuberances in form of a helix are desired, the distance between two threads should be small enough to induce reverse flow, as opposed to helical flow along the helix. As regards the shape of the protuberances, one can as well envisage the protuberance in the form of successive rings transverse to length direction of the medical device, either continuous or interrupted rings (continuous likely to be preferred). These rings could be manufactured also in a continuous casting or extrusion process by, for example, a spaced succession impulsive mechanical shocks applied to the die that forms the luminal wall surface, in the direction of advance of the extruded or cast strand each pulse corresponding to the creation of one annular protuberance.

In general, the protuberances may be formed continuously or discontinuously, being long-stretched or elongated (e.g. wave-like, spiral, helical, annular, oval etc.), rather short (e.g. point-like, rhombic, pyramidical, circular etc.), as well as any possible combination of elongated and short protuberances, and spaced apart at regular or irregular intervals. In either case, the elongated or long-stretched protuberances (such as wave-like protuberances) have to be arranged with their flank surfaces transversal to the direction of flow, that is, at an angle from about 1° and to about 90° transversal to the direction of flow. In one preferred embodiment, discrete protuberances are discontinuously formed into the shape of rhombi, which may be strictly rhombic or rounded rhomboidic elevations. Preferably, such discrete protuberances, such as rhombic protuberances, are arranged in lines of protuberances, and the protuberances of one line are located offset in a circumferential direction from the protuberances of the next adjacent line.

The protuberances may be formed into the wall surface, for example by removing material from the wall surface, or onto the wall surface, or by depositing material on top of the wall surface, or by forming such as stamping, or by attaching a structured foil to the wall surface. Removal of material could be accomplished by use of a cutting tool, laser or any other tool which is capable of removing material, and deposition of material could be carried into effect by spraying techniques or any other technique being suitable for material deposition.

Preferred materials for the medical device are e-PTFE, polyester such as DACRON®, polyester, PTFE, ePTFE, polyurethane, polyurethane-urea, siloxane, and combinations thereof, although any material suitable to be used as vessel-replacement material can be used.

BRIEF DESCRIPTION OF THE DRAWINGS

For a better understanding of the present invention, and to show more clearly how the same may be carried into effect, reference will now be made, by a way of an example only, to the accompanying drawings, in which

FIG. 7a shows a rotation disc suitable for forming the protuberances;

FIGS. 7b and 7c show a pattern of protuberances formed with the rotation disc shown in FIG. 7a;

FIG. 8a shows a rotation disc suitable for forming the protuberances;

FIGS. 8b and 8c show a pattern of protuberances formed with the rotation disc shown in FIG. 8a;

DETAILED DESCRIPTION OF PREFERRED EMBODIMENTS

The drawings attached hereto are schematic and not to scale.

Figure 1:
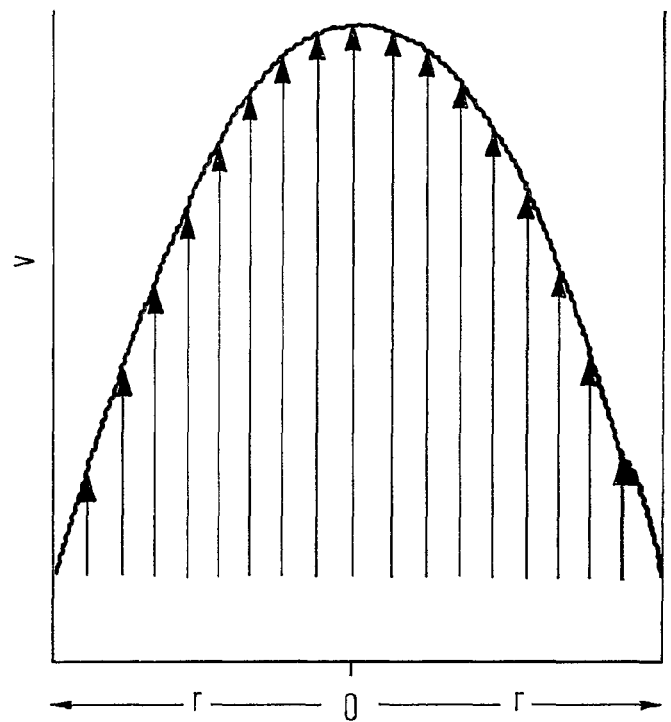
FIG. 1 shows a parabolic flow profile characteristic for laminar flow.

FIG. 1 has been explained already above.

Figure 2:
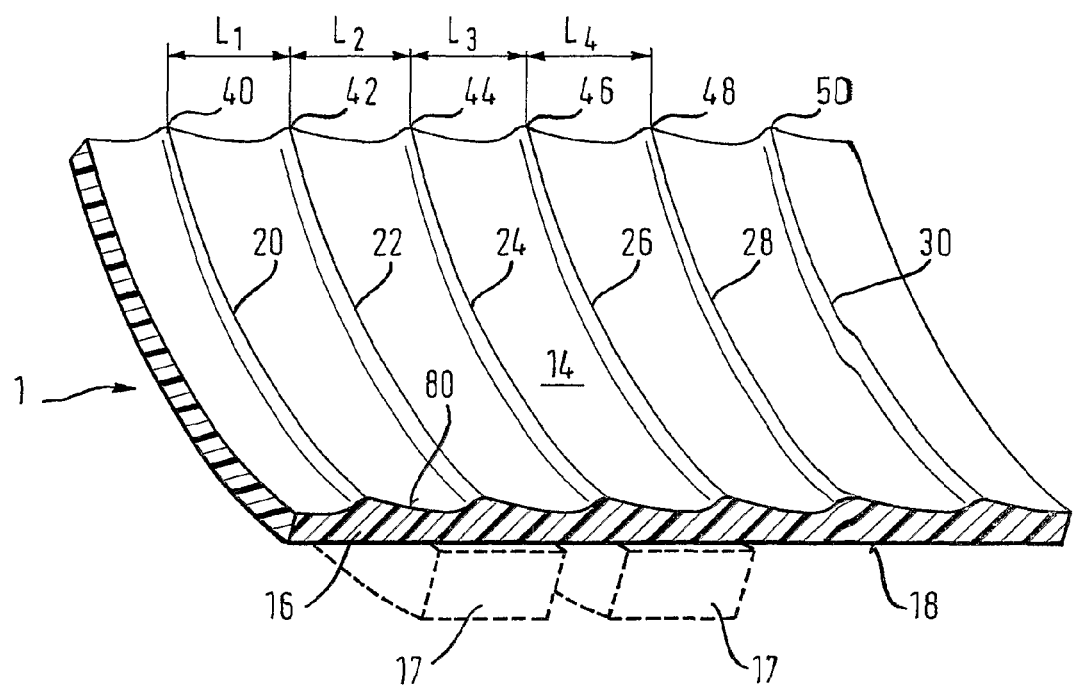
FIG. 2 shows an isometric view of part of the luminal wall surface of a graft for placement in a bodily lumen.

FIG. 2 shows an isometric view of a portion of the length of an e-PTFE cylindrical graft or tube 1. The present invention, however, is not limited to specific materials. Rather, any suitable material like e-PTFE or DACRON® can be used, depending only on the medical compatibility. For the sake of clarity, the drawing of FIG. 2 shows only a part of the circumference of the tube 1.

From FIG. 2 it can be seen that the luminal wall 14 of the tube, which marks the inside surface 80 of the wall thickness 16 of the tube, is itself not cylindrical, unlike the abluminal surface 18 of the tube, which is cylindrical. It is, however, contemplated that also the abluminal surface 18 of the tube does not necessarily have to be cylindrical. In addition, the overall form of the tube does not have to cylindrical, the tube can also have one or more branches, which themselves might have branches as well. Furthermore, the invention does not only relate to tubular implants, but also to non-tubular implants such as artificial cardiac prothesis, and extracorporally used devices.

Moving along the longitudinal axis of the tube 1, one crosses a succession of lines 20, 22, 24, 26, 28 and 30 of discontinuity, that are revealed as corresponding to cusps 40 to 50. As can be seen in FIG. 2, these cusps 40-50 are spaced at regular intervals along the length of the tube 1, and the line of discontinuity 20-30 associated with each respective cusp 40-50 is a line which is transverse to the longitudinal axis of the tube 1 and lying within a plane transverse to that axis. Depending on the form of the protuberances, they are not necessarily spaced at regular intervals, as explained above. Alternatively, the outer surface 18 can be coupled to a plurality of stent structures 17 to provide for a stent-graft.

Figure 3:
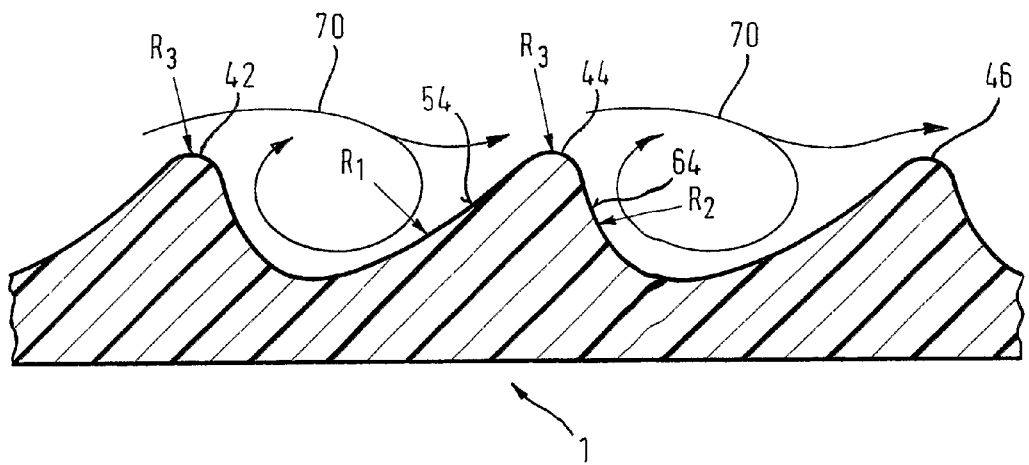
FIG. 3 shows a schematic cross-section of protuberances on the luminal wall surface.

Turning to the cross-section of FIG. 3 taken along the length of tube 1, one can see more clearly the surface shape of the luminal wall 14 of the tube 1 (see FIG. 2), in between the successive cusps 42, 44 and 46. More particularly, upstream of the cusp 44 (exemplarily defined by a radius of curvature R3) is a concave upstream flank surface 54 of that protuberance (exemplarily defined by radius of curvature R1) and immediately downstream of the cusp 44 is a downstream flank portion 64, also with an outwardly concave shape (exemplarily defined by a radius of curvature R2). There are corresponding upstream and downstream flank portions on each protuberance tipped by a cusp 40, 42, 46, 48 and 50 (not shown). Within the lumen of the tube 1 shown in FIG. 3, there are arrows which indicate the flow downstream from left to right in the drawing, with the long arrows 70 (length is not in proportion to flow velocity) indicating how the laminar flow strikes the upstream flank surface of each cusp and is reversed by it to track down the concave surface 54, from locations near the cusp 44 to locations closer to the generalized wall surface 80 of the tube 1 from which the protuberance is extended radially inwardly towards the axis of the lumen. Thus, arrows 70 show how the laminar downstream flow in the lumen of the tube 1 is converted, at the radially outermost portions of the lumen, by the upstream facing flanks such as 54 of the cusps such as 44, into a laminar flow upstream, along the luminal wall surface 80 as far as the next upstream adjacent downstream facing flank surface, such as 64, of the next upstream cusp.

It will be appreciated from FIG. 2 that there are ranges of spacings L1, L2, L3, L4 and so on between adjacent cusps along the length of a tube, which can be configured to produce the desired upstream laminar flow along the luminal wall surface 80 between adjacent cusps, and to avoid zones of stagnant fluid, or zones of turbulent flow. With efficient design, the luminal wall surface 80 is overall bathed in a unidirectional laminar flow which, paradoxically, is in the opposite direction to the generalized laminar flow downstream through the lumen of the tube. It should be noted that while the spacings are shown as being equal, an alternative embodiment can be provided in which the spacings are not equal or that they may be equal for some cusps and may not be equal for other cusps.

Figure 4:
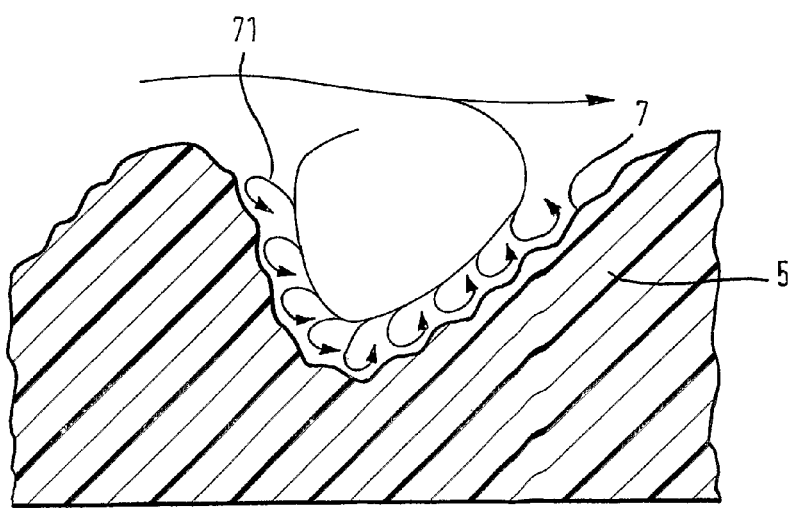
FIG. 4 shows a schematic cross-section of a luminal wall surface having primary and secondary structures.

FIG. 4 shows another embodiment of the medical device of the present invention. In this embodiment, successive protuberances additionally comprise a second, smaller surface structure. That is, the successive protuberances can be considered as a primary or macro-structure 5, and said additional surface structure can be considered as a secondary or micro-structure 7. The micro-structure 7 overlies the macro-structure 5, thus, additionally creating smaller micro-vortices, indicated by arrows 71. These smaller micro-vortices overlie the reversed flow in between two successive cusps to further disturb the stasis of the layer adjacent to the luminal wall. Thereby, the retention time of blood cells prone to adhesion in the marginal zone can be further reduced. The micro-structure 7 may comprise micro-protuberances with a height from about 10 to about 50 μm. The distance between two adjacent micro-protuberances of the micro-structure 7 may be in the range of 20 to about 100 μm. As regards the specific design of said micro-protuberances of the micro-structure 7, it is contemplated that these micro-protuberances may have the same external shape and form as the protuberances of the macro-structure 5, just being smaller in size.

The drawing figures show only two possible embodiments and skilled readers will recognize that many other embodiments are feasible, which take advantage of the inventive concept.

As mentioned before, the medical devices of the present invention can be produced by e.g. extrusion, axial stretching or sintering. However, any other suitable process can be used as well, as long as the structure of the inventive implants can be satisfactorily created, and the desired effect is achieved.

Figure 5:
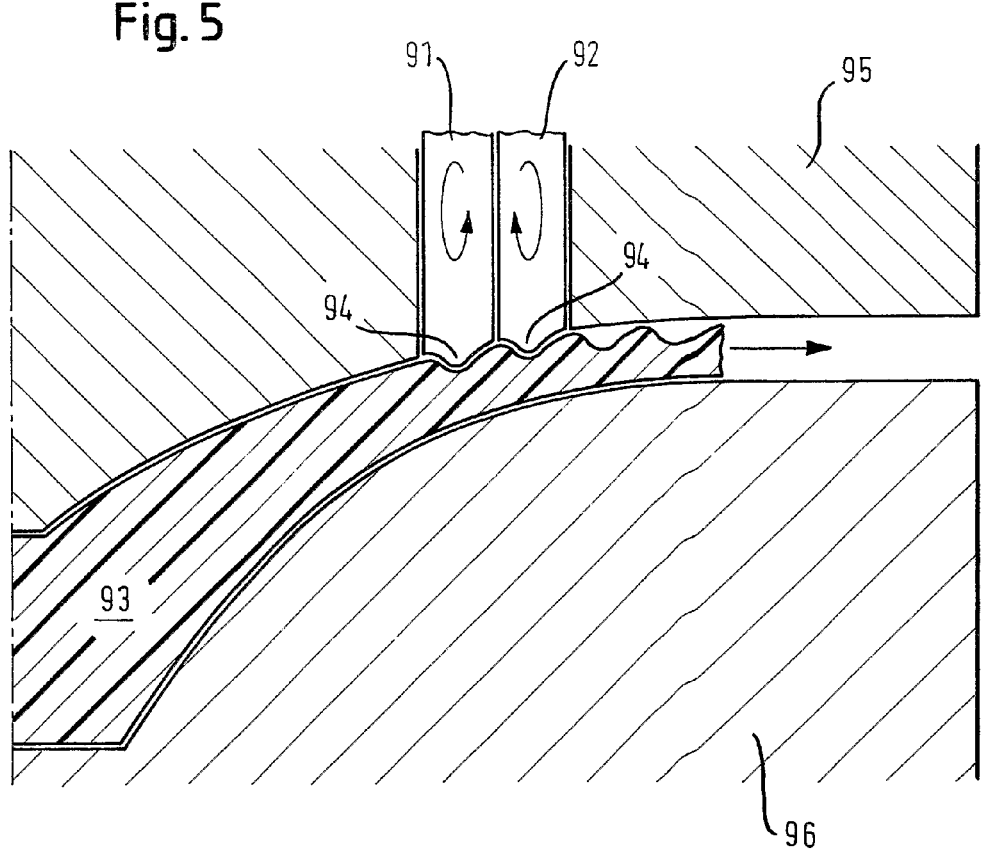
FIG. 5 shows the production of a graft simultaneously with protuberances.

It is contemplated that a luminal wall topography such as is shown in the drawings could be accomplished by imposing on the extrusion die a succession of mechanical impulses or "jogs" each one of which would correspond to formation of one of the protuberances visible in the drawing figures, each tipped by a cusp 40 to 50. However, again, those skilled in the art will be able to visualize variations. An important one could be the continuous formation of a wave-like thread-form protuberance on the luminal wall 14 of a tube 1, created by a forming tool immediately downstream of an extrusion die. The forming tool might as well constitute part of the extruder, as shown in FIG. 5. The tool can rotate relative to the tube 1 at a speed of rotation that is coordinated with the axial downstream rate of movement of the extrudate such as to set up the desired pitch of the helical thread so that there is the desired spacing between adjacent protuberances. Thereby a transverse section similar to that shown in FIG. 2, but with the upper half of the section axially displaced relative to the lower half of the section by a distance of half the distance between two adjacent cusps as shown in FIG. 2, is yielded.

Figure 7:
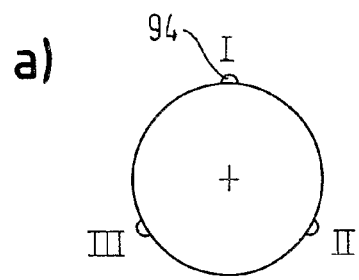
Figure 7:
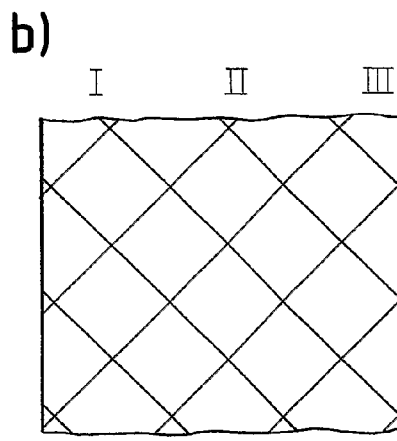
Figure 7:
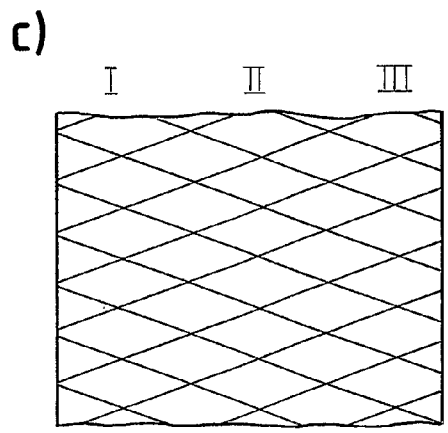
Figure 8:
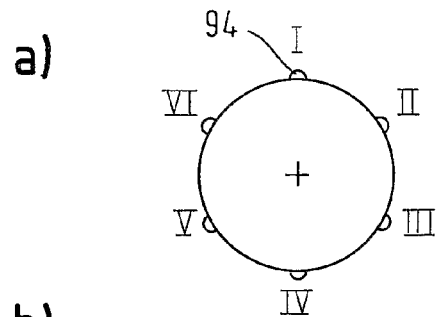
Figure 8:
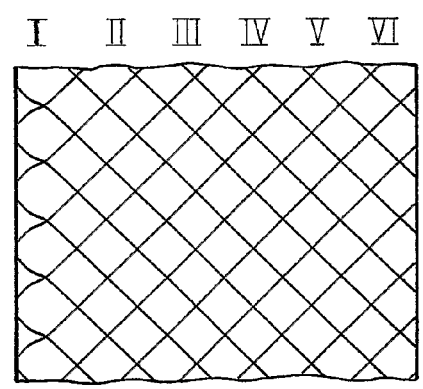
Figure 8:
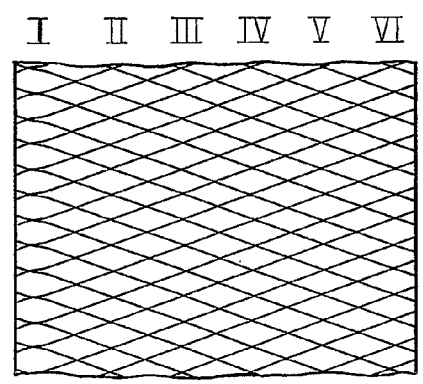

In FIG. 5 the making of a medical device according to the present invention with two forming tools is shown. The extrusion die comprises the two rotating forming tools or rotation discs 91, 92 as well as an inner 95 and an outer 96 mandrel. The two rotating forming tools 91, 92 of the extrusion die rotate in opposite directions at a speed which is coordinated with the axial downstream rate of movement of the extrudate 93. In FIGS. 7a and 8a different rotation discs or forming tools 91, 92 are shown. The forming tool shown in FIG. 7a comprises three protrusions 94, which are also indicated in FIG. 5. By means of the two forming tools 91, 92, each having three protrusions 94 and rotating in opposite directions, the patterns of protuberances shown in FIGS. 7b, c can be obtained. The pattern shown in FIG. 7b is obtained with a relatively slower rotational speed, whereas the pattern shown in FIG. 7c is obtained with a relatively higher rotational speed. The forming tool or rotation disc shown in FIG. 8 has six protrusions 94, leading to a pattern as shown in FIGS. 8b, c. FIG. 8c showing a pattern obtained with a relatively higher opposite rotational speed of the forming tools 91, 92 and FIG. 8b showing a pattern obtained with a relatively slower rotational speed.

Although undulations in the form of a periodic generally sinusoidal pattern has been shown, it is also intended that other suitable structures that can generate flow vortices near the surface of the graft to ensure laminar flow above the surface of the graft be utilized. Such suitable structures may include dimples formed into or out of the surface of the graft. Alternatively, vortex generators can be disposed at various positions on the blood-contacting surface of the prosthetic implant device (e.g., graft or stent-graft (polymeric encapsulated stent)) so as to maintain a laminar flow condition just slightly above the surface of the blood-contacting surface. And laminar flow through the prosthetic device can be inferred by the Reynolds number for the fluid (e.g., blood having an average density of about 1.05 g/cm$^3$ and an average viscosity of about $\frac{1}{30}$ poise with a suitable level of tolerance in the values to account for biological variations) flowing through the prosthetic implant device. Depending on the inside diameter of the prosthetic device 1, the Reynolds number can be less than or equal to about 0.0025; less than or equal to about 0.03; or less than or equal to about 2000.

Figure 6:
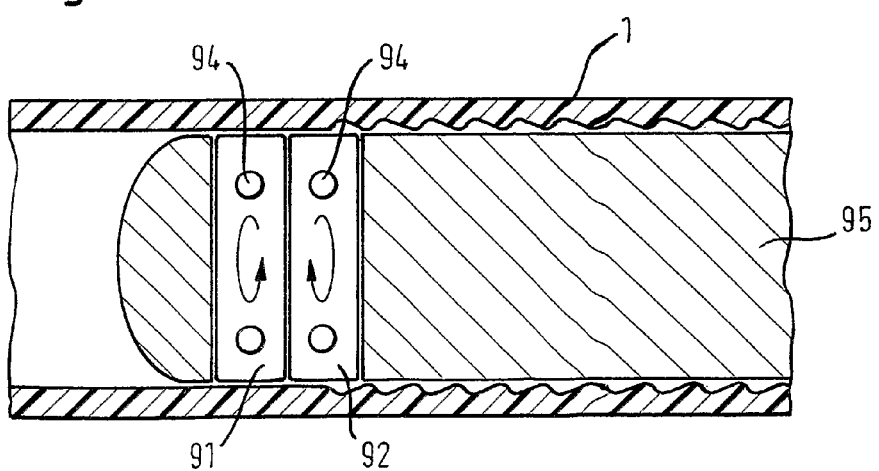
FIG. 6 shows one method of the making of protuberances after having formed the graft.

In FIG. 6 the formation of protuberances subsequent to the formation of the device (tube 1) is shown. As can be seen from FIG. 6, the forming device comprises two forming tools 91, 92, each having an arbitrary number of protrusions 94, and an inner mandrel 95. While each of the forming tools 91, 92 is rotating in an opposite direction, the tube 1 is being pressed over the mandrel 95, the rotational speed of the forming tools 91, 92 being coordinated relative to the axial velocity of movement of the tube 1, thereby forming the protuberances in the luminal wall of the tube at desired intervals. As is evident for the skilled person, the spacing between two adjacent protuberances and their form can be easily adjusted and adapted to the desired task, by adapting the rotational speed of the rotation discs 91, 92, whereby the rotational speed of two oppositely rotating discs does not necessarily have to be equal. In addition, also less, e.g. one, or more, e.g. three, forming tools can be used, whereby each of the forming tools can rotate in a first or a second direction and with a first or second or third etc. velocity, depending on the pattern intended to achieve. Instead of rotating the respective tool (s), however, also the tube can be rotatively advanced over a fixedly positioned tool. It is also contemplated that the protrusions of the forming tools are structured, so as to simultaneously from macro- and micro-structures.

The methods for the production of the medical device of the present invention described above involve forming of the desired structure in the lumen, either during or after forming of the medical device as such. However, further methods for the production of the inventive medical device are envisaged, which involve the "inversion" of the prosthesis. In particular, in these methods, after the device had been formed, the initial luminal surface of the device becomes the abluminal surface, whereas the initial abluminal surface of the device becomes its luminal surface.

Figure 9:
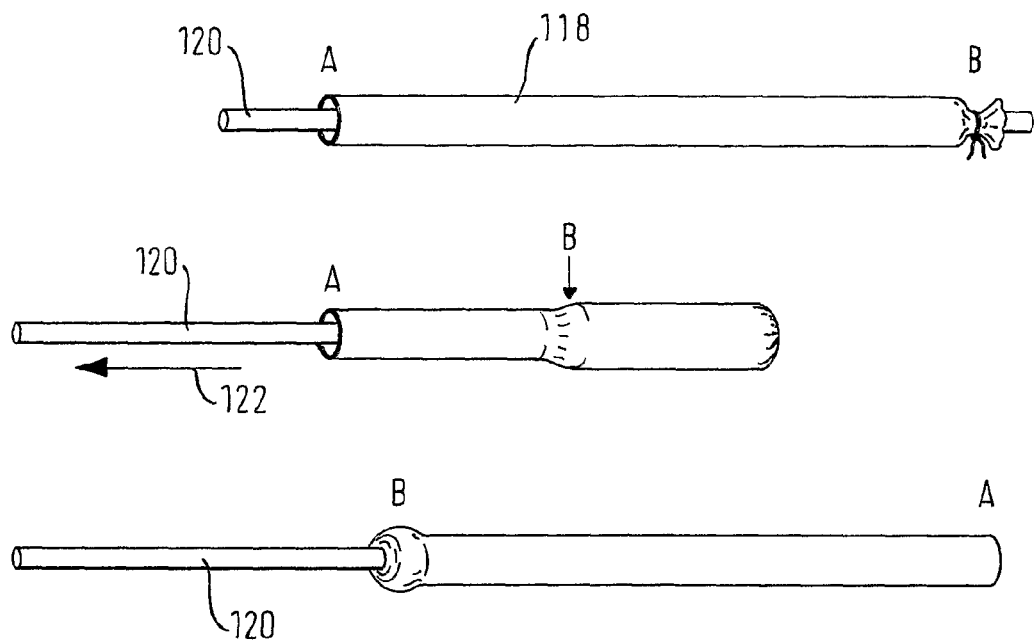
FIG. 9 shows the step of inverting the prothesis.

The step of "inverting" of a prosthesis is schematically shown in FIG. 9. For the inversion, one end B of the prosthesis 118 is fixed on a mandrel or rod 120, and the rod with the affixed end B is drawn in the direction of the other end of the prosthesis A, indicated by the arrow 122 in FIG. 9, thereby turning the inside of the prosthesis out. Although not shown, it is also possible that the prosthesis 118 is inverted by drawing the end A over the prosthesis towards and over the end B. In any event, when the medical device is inverted, the desired structure can be formed on the thereby exposed abluminal radially outer surface. After having formed the desired structure on the surface, the prosthesis will be inverted again, so that the structure then lies on the inside or lumen of the prosthesis.

Figure 10:
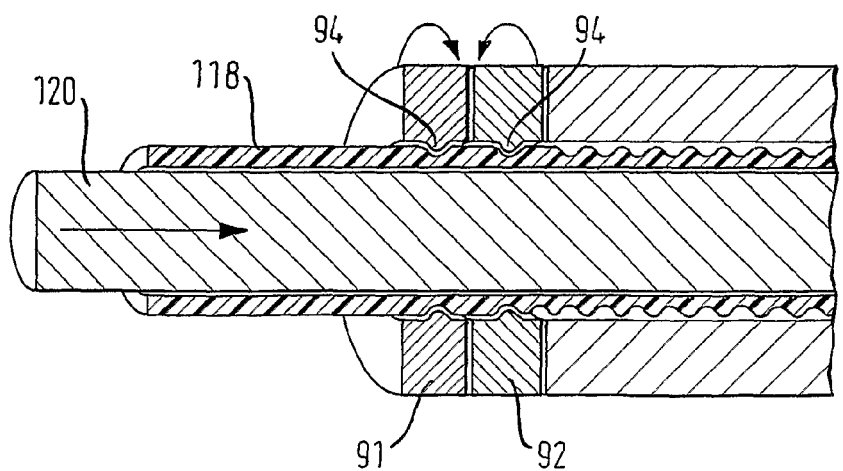
FIG. 10 shows an alternative method of making of protuberances after having formed the graft.

The desired structure on the outer surface of a prosthesis, which had been inverted as described above, can be formed by any means known by those skilled in the art. For instance, the desired surface structure can be formed by means of a laser, or any other suitable cutting and/or non-cutting tool. As will be apparent for the skilled person, pressure and temperature of the forming tool will be adapted to the material used. Preferably, during forming of the surface structure, the inverted prosthesis 118 is lying on and close to the rod 120 which had been used for the inversion. As shown in FIG. 10, the structure may be formed with a tool having two counter-rotating forming tools 91, 92. Each forming tool 91, 92 comprises protrusions 94 for forming of the desired surface structure, similar to the forming tools 91, 92 shown in FIG. 6. In this production method, however, the prosthesis 118 lying closely on the rod 120 is fed by the rod through the tool, whereby the desired surface pattern is obtained.

Figure 11:
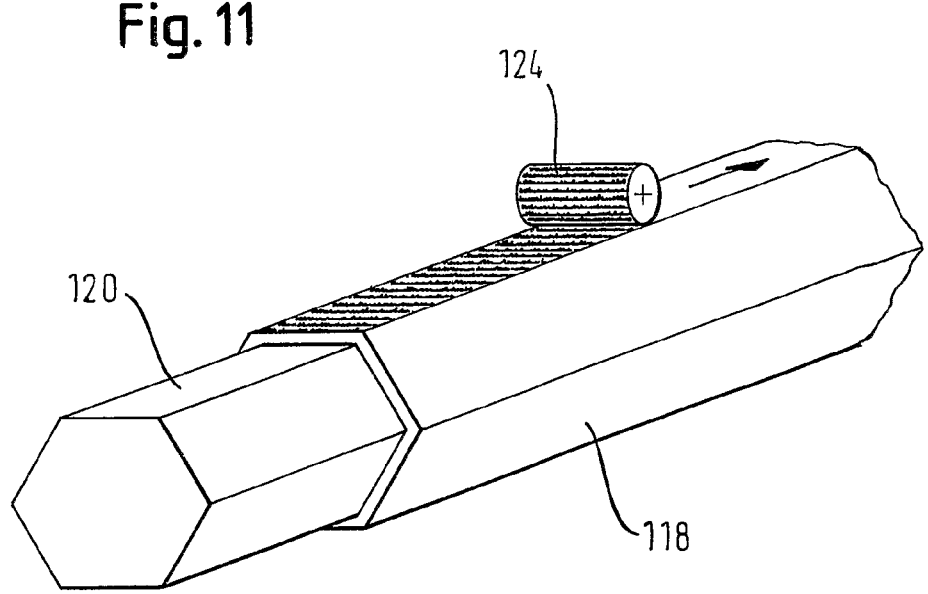
FIG. 11 shows another alternative method of making of protuberances after having formed the graft.
Figure 12:
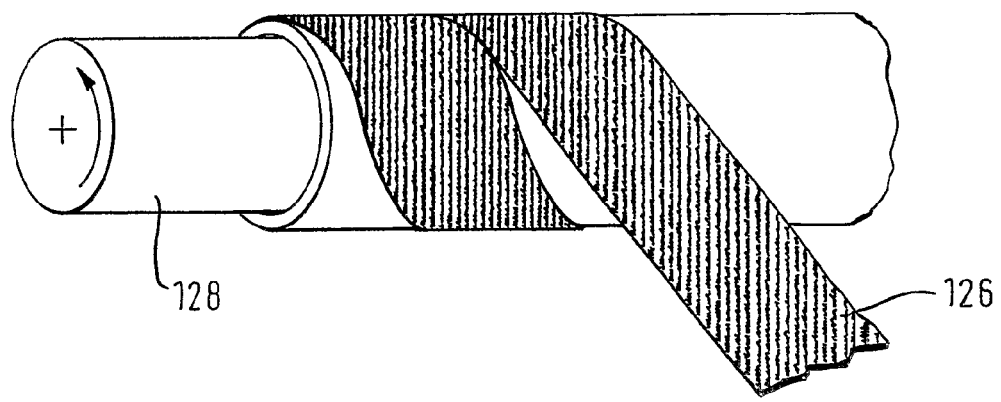
FIG. 12 shows the step of attaching a relief-bearing foil to a prothesis.

Further alternative production methods are shown in FIGS. 11 and 12. In the method shown in FIG. 11, the desired pattern is formed by means of a roller 124 having a structured surface. The roller is advanced under pressure over the surface of the prosthesis 118 to form the desired pattern. For ease of forming of the surface structure on the prosthesis, the roller can be heated and/or the prosthesis can be heated, either directly or by means of heating the rod 120 on which it lies. The rod, which is stabilizing the prosthesis during forming of the surface structure, may have a circular or preferably a polygonal cross-section, such as hexagonal as shown in FIG. 11. However, the rod may have any cross-section, dimension and overall form which is suitable for counteracting efficiently with a roller. It is also intended that one would attach a textured sheet or foil 126, bearing the desired pattern, to the outside of the inverted prosthesis, such as in a continuous spiral, as shown in FIG. 12, in which the prosthesis 118 is mounted on a driven roller 128.

While the application of the invention envisaged by the present inventor to be primary interest is tubes for use as grafts and other bodily implants within a lumen of the human body that is carrying a blood flow, other applications will be evident to those readers that are concerned with particular deposition problems from particular fluids. Furthermore, various drugs or bio-active agents can be incorporated into the inner or outer surface of the prosthetic implantable medical device (e.g., grafts or encapsulated stents). The drugs or bio-active agents include but are not limited to: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), calcium salts such as hydroxyapatite that does not promote bone formation; silver particles and silver chloride ions; purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The invention claimed is:

1. A graft configured for implantation in a human or animal body which defines a lumen for flowing a bodily fluid from an upstream end of the graft to a downstream end thereof, the graft having a luminal wall that extends between the upstream and downstream ends and defines the lumen within which the fluid flows, the luminal wall comprising a succession of protuberances spaced from each other along the length of the graft, each protuberance having a flank facing upstream and a flank facing downstream, the flank facing upstream extending into the fluid flow so that a radially outermost part of the flow of fluid from the upstream to the downstream end of the graft impinges on the upstream flank and is thereby caused to reverse its flow and flow upstream from the upstream flank to the downstream flank of an adjacent protuberance upstream, creating micro-vortices between adjacent protuberances.

2. The graft according to claim 1, wherein the bodily fluid is blood.

3. The graft according to claim 1, wherein the protuberances are contiguous.

4. The graft according to claim 1, wherein the protuberances are discrete and separate from one another.

5. The graft according to claim 1, wherein the protuberances are symmetrical, in that the downstream flank is a minor image of the upstream flank.

6. The graft according to claim 5, wherein the upstream flank and the downstream flank each comprise an outwardly concave portion.

7. The graft according to claim 1, wherein the protuberances are asymmetrical, in that a downstream flank profile is different from an upstream flank profile.

8. The graft according to claim 7, wherein the upstream flank has a more shallow gradient than the downstream flank.

9. The graft according to claim 1, wherein at least one of the upstream flank and the downstream flank exhibits a portion of constant gradient.

10. The graft according to claim 1, wherein wall surfaces of the upstream flank and the downstream flank meet at a cusp.

11. The graft according to claim 1, wherein a transition between the luminal wall and the upstream flank and/or downstream flank is that of an essentially exponential curve.

12. The graft according to claim 1, wherein adjacent protuberances have essentially the same height.

13. The graft according to claim 1, wherein adjacent protuberances have different heights.

14. The graft according to claim 1, wherein each protuberance extends into the lumen by a distance of about 10% of the diameter of the lumen.

15. The graft according to claim 1, wherein the height of each protuberance is from about 0.02 mm to about 2 mm.

16. The graft according to claim 1, wherein a distance between adjacent protuberances is from about 1 times to about 10 times the height of the protuberance.

17. The graft according to claim 1, wherein the protuberances are equidistantly spaced along the lumen.

18. The graft according to claim 1, wherein a distance between adjacent protuberances varies along the lumen.

19. The graft according to claim 1, wherein the protuberances have a wave-like form when viewed in section through the long axis of the lumen.

20. The graft according to claim 1, wherein the protuberances have a rhombic form when viewed in section through the long axis of the lumen.

21. The graft according to claim 1, wherein the protuberances are arranged relative to each other on a helical locus that winds around the lumen.

22. The graft according to claim 1, wherein micro-protuberances are formed on the surface of one or more of the protuberances.

23. The graft according to claim 22, wherein the height of the micro-protuberances is from about 10 μm to about 50 μm.

24. The graft according to claim 22, wherein a distance between adjacent micro-protuberances is from about 20 μm to about 100 μm.

25. The graft according to claim 1, wherein the surface area of the upstream and downstream flanks comprises a portion with a nano-topography suitable to foster a Lotus-effect.

26. The graft according to claim 1, wherein the graft is an artificial blood vessel.

27. The graft according to claim 1, wherein the protuberances comprise expanded polytetrafluoroethylene (e-PTFE).

28. The graft according to claim 1, wherein the protuberances comprise polyester.

29. The graft according to claim 1, wherein the height of each protuberance is from about 0.05 mm to about 1 mm.

30. The graft according to claim 1, wherein a distance between two adjacent protuberance is from about 2 times to about 6 times the height of the protuberance.

31. An artificial heart configured for implantation in a human or animal body which defines a lumen for flowing a bodily fluid from an upstream end of the artificial heart to a downstream end thereof, the artificial heart having a luminal wall that extends between the upstream and downstream ends and defines the lumen within which the fluid flows, the luminal wall comprising a succession of protuberances spaced from each other along the length of the artificial heart, each protuberance having a flank facing upstream and a flank facing downstream, the flank facing upstream extending into the fluid flow so that a radially outermost part of the flow of fluid from the upstream to the downstream end of the artificial heart impinges on the upstream flank and is thereby caused to reverse its flow and flow upstream from the upstream flank to the downstream flank of an adjacent protuberance upstream, creating micro-vortices between adjacent protuberances.

* * * * *